(12) United States Patent
Castelli et al.

(10) Patent No.: US 7,439,398 B2
(45) Date of Patent: *Oct. 21, 2008

(54) ENANTIOMERICALLY PURE ATOMOXETINE AND TOMOXETINE MANDELATE

(75) Inventors: Eugenio Castelli, Arlate di Calco (Lecco) (IT); Paola Daverio, Villasanta (MI) (IT); Silvia Mantovani, Cesano Maderno (MI) (IT)

(73) Assignee: Teva Pharmaceutical Fine Chemicals S.R.L., Bulciago (LC) (IT)

( * ) Notice: Subject to any disclaimer, the term of this patent is extended or adjusted under 35 U.S.C. 154(b) by 39 days.

This patent is subject to a terminal disclaimer.

(21) Appl. No.: 11/170,378

(22) Filed: Jun. 28, 2005

(65) Prior Publication Data

US 2006/0009490 A1  Jan. 12, 2006

Related U.S. Application Data

(60) Provisional application No. 60/583,641, filed on Jun. 28, 2004, provisional application No. 60/609,716, filed on Sep. 14, 2004, provisional application No. 60/622,065, filed on Oct. 25, 2004, provisional application No. 60/652,330, filed on Feb. 11, 2005, provisional application No. 60/583,644, filed on Jun. 28, 2004, provisional application No. 60/652,332, filed on Feb. 11, 2005, provisional application No. 60/583,643, filed on Jun. 28, 2004, provisional application No. 60/652,331, filed on Feb. 11, 2005, provisional application No. 60/666,666, filed on Mar. 30, 2005, provisional application No. 60/675,369, filed on Apr. 26, 2005, provisional application No. 60/689,778, filed on Jun. 9, 2005, provisional application No. 60/690,738, filed on Jun. 14, 2005.

(51) Int. Cl.
C07C 217/62 (2006.01)
C07C 213/10 (2006.01)
A61K 31/135 (2006.01)

(52) U.S. Cl. .................. 564/347; 514/651
(58) Field of Classification Search .............. None
See application file for complete search history.

(56) References Cited

U.S. PATENT DOCUMENTS 4,018,895 A  4/1977  Molloy et al.
4,777,291 A  10/1988  Misner
4,868,344 A  9/1989  Brown
5,658,590 A  8/1997  Heiligenstein et al.
6,333,198 B1  12/2001  Edmeades et al.
6,541,668 B1  4/2003  Kjell et al.

FOREIGN PATENT DOCUMENTS

| DE | 41 23 253 A1 | 1/1993 |
|---|---|---|
| EP | 0 052 492 A1 | 5/1982 |
| EP | 0 193 405 A1 | 9/1986 |
| EP | 0 721 777 A2 | 1/1995 |
| WO | WO 94/00416 | 1/1994 |
| WO | WO 00/58262 | 11/2000 |
| WO | WO 00/64855 | 11/2000 |
| WO | WO 2006-004976 A2 | 1/2006 |
| WO | WO 2006/004977 A2 | 1/2006 |
| WO | WO 2006/004979 A2 | 1/2006 |
| WO | WO 2006/020348 A2 | 2/2006 |
| WO | WO 2006/068662 A1 | 6/2006 |

OTHER PUBLICATIONS

Anon (R)-(-)-(N)-Methyl-3-(2-Methylphenoxy)Phenyl-3-Phenylpropylamine (S)-(+)-Mandelate Chemical Abstracts Service XP-002367856 Dec. 29, 2004.
Koenig, T.M. et al. "A Convenient Method for Preparing Enantiomerically Pure Norfluoxetine, Fluoxetine and Tomoxetine" Tetrahedron Letters, vol. 35, No. 0, pp. 1339-1342 (1994).
Strobel, H.A.; Heineman, W.R., Chemical Instrumentation: A Systematic Approach, 3rd dd. (Wiley & Sons: New York 1989)—pp. 391-393, 879-894, 922-925, 953.
Snyder, L.R.; Kirkland, J.J., Introduction to Modern Liquid Chromatography, 2nd ed. (John Wiley & Sons: New York 1979)—pp. 549-552, 571-572.
Srebnik, M. et al. "Chiral Synthesis via Organoboranes. 18. Selective Reductions. 43. Dissopinocampheylchloroborane as an Excellent . . . " J. Org. Chem. (1988), vol. 53, p. 2916-2920.
Sellers, J.A. et al. "Determination of the Enantiomer and Positional Isomer Impurities in Atomoxetine Hydrochloride with Liquid Chromatography Using Polysaccharide Chiral Stationary Phases." J. of Pharmaceutical and Biomedical Analysis, vol. 41, pp. 1088-1094 (2006).

*Primary Examiner*—Brian J Davis
(74) *Attorney, Agent, or Firm*—Kenyon & Kenyon LLP

(57) ABSTRACT

The present invention provides enantiomerically pure (R)-(-)-tomoxetine (S)-(+)-mandelate and atomoxetine HCl. The present invention further provides enantiomerically pure (R)-(-)-tomoxetine (S)-(+)-mandelate prepared from racemic tomoxetine. The present invention also provides enantiomerically pure atomoxetine HCl prepared from (R)-(-)-tomoxetine (S)-(+)-mandelate.

29 Claims, No Drawings

ENANTIOMERICALLY PURE ATOMOXETINE AND TOMOXETINE MANDELATE

CROSS-REFERENCE TO RELATED APPLICATIONS

This application claims the benefits of U.S. Provisional Patent Application Nos. 60/583,641, filed Jun. 28, 2004, 60/609,716, filed Sep. 14, 2004, 60/622,065, filed Oct. 25, 2004, 60/652,330, filed Feb. 11, 2005, 60/583,644, filed Jun. 28, 2004, 60/652,332, filed Feb. 11, 2005, 60/583,643, filed Jun. 28, 2004, 60/652,331, filed Feb. 11, 2005, 60/666,666, filed Mar. 30, 2005, 60/675,369, filed Apr. 26, 2005, 60/689,778, filed Jun. 9, 2005, and 60/690,738, filed Jun. 14, 2005, the contents of all of which are incorporated herein by reference.

FIELD OF THE INVENTION

The present invention relates enantiomerically pure atomoxetine and tomoxetine mandelate obtained after an optical resolution of racemic tomoxetine.

BACKGROUND OF THE INVENTION

Atomoxetine HCl is a selective norepinephrine reuptake inhibitor. It is marketed under the name STRATTERA® for the treatment of Attention-Deficit/Hyperactivity Disorder (ADHD) and is available in 10 mg, 18 mg, 25 mg, 40 mg, and 60 mg dosage forms.

Atomoxetine, chemically known as (R)(-)—N-methyl-3-(2-methylphenoxy)-3-phenylpropylamine, has the following structure:

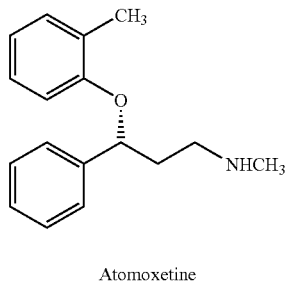

Atomoxetine

Atomoxetine, the (R)-(-) enantiomer of tomoxetine, is an aryloxyphenylpropylamine. It is about twice as effective as the racemic mixture and about nine times more effective than the (+)-enantiomer, as disclosed in U.S. Pat. No. 4,018,895 (assigned to Eli Lilly and Co.), EP 0 052 492 (Eli Lilly and Co.), and EP 0 721 777 (Eli Lilly and Co.).

Optical resolution of racemic tomoxetine into (R)-(-)-tomoxetine (atomoxetine) and (S)-(+)-tomoxetine is known in the art both by chiral chromatography and fractional crystallization of (S)-(+)-mandelic acid diastereoisomeric addition salts.

The EP '492 patent describes a resolution process wherein racemic tomoxetine, prepared from N-methyl-3-hydroxy-3-phenylpropylamine, is resolved with (S)-(+)-mandelic acid to obtain (R)-(-)-tomoxetine (S)-(+)-mandelate salt in a poor yield of about 18%. This process is rather tedious and burdened by environmentally unfriendly solvents like diethyl ether and dichloromethane. Moreover, although it is known in the art that theoretical upper limit for yield in such optical resolution is 50%, the declared yield is rather low.

Subsequently, atomoxetine HCl may be prepared from (R)-(-)-tomoxetine (S)-(+)-mandelate by processes such as the one disclosed in EP Patent No. 0 052 492. In this process, (R)-(-)-tomoxetine (S)-(+)-mandelate is first basified in water to eliminate the mandelate, then extracted in diethyl ether. HCl gas is bubbled into the solution to obtain (R)-(-)-tomoxetine (atomoxetime) hydrochloride.

During the processes described above, a large amount of the racemic tomoxetine is lost in mother liquors as (S)-(+)-tomoxetine, the unwanted enantiomer. This is not advantageous from a commercial point of view, and the desired enantiomer is contaminated with the undesired (S)-(+)-tomoxetine enantiomer. In order to get the desired isomer, the final product requires purification by tedious and cumbersome purification processes such as column chromatography, HPLC or other techniques, thus making the approach commercially difficult to implement.

Enantiomeric purity studies performed on the commercial tablet, STRATTERA® 60 mg, showed that it contains the (S)-(+)-tomoxetine enantiomer at a level of 0.28% area by HPLC.

Stereochemical purity is of importance in the field of pharmaceuticals, where many of the most prescribed drugs exhibit chirality, and the two isomers exhibit different potency. Furthermore, optical purity is important since certain isomers may actually be deleterious rather than simply inert. Therefore, there's a need to obtain the desired enantiomer of atomoxetine HCl in high enantiomeric purity.

Additionally, in order to achieve a high efficiency of reaction for industrial scale synthesis of atomoxetine HCl, it is necessary to minimize the enantiomeric impurities, and obtain the desired isomer in high yields and a high optical purity.

SUMMARY OF THE INVENTION

In one embodiment, the present invention encompasses enantiomerically pure (R)-(-)-tomoxetine (S)-(+)-mandelate, wherein the level of the (S)-(+)-tomoxetine (S)-(+)-mandelate enantiomer is about 0.1% or less. Preferably, the level of the (S)-(+)-tomoxetine (S)-(+)-mandelate enantiomer is about 0.08% or less. More preferably, the level of the (S)-(+)-tomoxetine (S)-(+)-mandelate enantiomer is about 0.07% or less.

In another embodiment, the present invention encompasses enantiomerically pure atomoxetine hydrochloride (HCl), wherein the level of the (S)-(+)-tomoxetine enantiomer is about 0.1% or less. Preferably, the level of the (S)-(+)-tomoxetine enantiomer is about 0.03% or less. More preferably, the level of the (S)-(+)-tomoxetine enantiomer is about 0.01% or less.

In yet another embodiment, the present invention encompasses enantiomerically pure (R)-(-)-tomoxetine (S)-(+)-mandelate obtained by optical resolution of racemic tomoxetine.

The present invention further encompasses enantiomerically pure atomoxetine HCl, obtained by converting the enantiomerically pure (R)-(-)-tomoxetine (S)-(+)-mandelate obtaind as described above, into atomoxetine HCl.

DETAILED DESCRIPTION OF THE INVENTION

The present invention provides enantiomerically pure atomoxetine hydrochloride (HCl) and (R)-(-)-tomoxetine (S)-(+)-mandelate.

The term "enantiomerically pure", in reference to atomoxetine HCl and (R)-(−)-tomoxetine (S)-(+)-mandelate, means having less than about 0.1% of the respective undesired enantiomer.

The term "crude (R)-(−)-tomoxetine (S)-(+)-mandelate" refers to a preparation of (R)-(−)-tomoxetine (S)-(+)-mandelate wherein the level of (S)-(+)-tomoxetine (S)-(+)-mandelate enantiomer is more than about 0.1%.

The present invention provides (R)-(−)-tomoxetine (S)-(+)-mandelate wherein the level of the (S)-(+)-tomoxetine (S)-(+)-mandelate enantiomer is about 0.1% or less. Preferably, the level of the (S)-(+)-tomoxetine (S)-(+)-mandelate enantiomer is about 0.08% or less. More preferably, the level of the (S)-(+)-tomoxetine (S)-(+)-mandelate enantiomer is about 0.07% or less.

The present invention further provides atomoxetine HCl wherein the level of the (S)-(+)-tomoxetine is about 0.1% or less. Preferably, the level of the (S)-(+)-tomoxetine enantiomer is about 0.03% or less. More preferably, the level of the (S)-(+)-tomoxetine enantiomer is about 0.01% or less.

The present invention provides enantiomerically pure (R)-(−)-tomoxetine (S)-(+)-mandelate obtained by a process of optical resolution of racemic tomoxetine. This process comprises combining racemic tomoxetine and (S)-(+)-mandelic acid in the presence of a $C_{1-4}$ alcohol and an aromatic hydrocarbon, to obtain a reaction mixture. Preferably, the $C_{1-4}$ alcohol is methanol. Preferably, the aromatic hydrocarbon is a $C_6$ to $C_{10}$ aromatic hydrocarbon optionally substituted with one or more (preferably one to three) $C_1$ to $C_3$ alkyl groups, $C_3$ to $C_8$ alkyl esters and $C_3$ to $C_8$ alkyl ethers, such as benzene, xylene, or toluene. Most preferably, the aromatic solvent is toluene. The reaction mixture is preferably heated to dissolve any undissolved solids. The reaction mixture may be heated to between 60° C. and 80° C., more preferably, between 65° C. and 70° C., most preferably to about 65° C. Upon lowering the temperature, crude (R)-(−)-tomoxetine (S)-(+)-mandelate solidifies, and is recovered from the reaction mixture. Preferably, the temperature is lowered to between 55° C. and 0° C., more preferably between 45° C. and 0° C. Most preferably, the temperature is initially lowered to about 45° C., and then to about 0° C. A most preferred crystallization temperature is about 0° C.

The present invention provides enantiomerically pure atomoxetine HCl, obtained by the process of converting enantiomerically pure (R)-(−)-tomoxetine (S)-(+)-mandelate into atomoxetine HCl. This process comprises combining enantiomerically pure (R)-(−)-tomoxetine (S)-(+)-mandelate and an organic solvent in the presence of water and a base, and then with HCl, either as gas or as an aqueous solution.

Preferably, the organic solvent is a $C_{1-4}$ alkyl ester, most preferably n-butyl acetate. Preferably, the base is selected from an alkali metal hydroxide, such as NaOH or KOH, or an alkali metal carbonate such as $Na_2CO_3$ or $K_2CO_3$. Most preferably, the base is NaOH. The reaction is preferably performed at a temperature between about 15° C. and 40° C. Most preferably, the reaction is performed at a temperature of about 20° C. and 25° C.

The enantiomerically pure atomoxetine HCl disclosed herein may be prepared as a pharmaceutical composition that is believed to be useful for the treatment of attention deficit disorder. Such composition includes atomoxetine HCl or the pharmaceutically acceptable carriers and/or excipients known to one of skill in the art.

Also provided by the present invention is the use of enantiomerically pure (R)-(−)-tomoxetine (S)-(+)-mandelate in the preparation of atomoxetine hydrochloride.

For example, this composition may be prepared as a medicament to be administered orally, parenterally, rectally, transdermally, bucally, or nasally. Suitable forms for oral administration include tablets, compressed or coated pills, dragees, sachets, hard or gelatin capsules, sublingual tablets, syrups and suspensions. Suitable forms of parenteral administration include: aqueous, or non-aqueous solutions or emulsions, while the rectal administration suitable form for administration includes suppositories with hydrophilic or hydrophobic vehicle. The topical administration of the invention provides suitable transdermal delivery systems known in the art, and for nasal delivery there are provided suitable aerosol delivery systems known in the art.

EXAMPLES

Chiral HPLC Analysis
Instrument: HPLC Hewlett Packard VWD detector HP1100
Column: CHIRACEL OD-R cellulose tris (3,5-dimethylphenylcarbamate) 250 mm×4.60 mm×10 mm (Daicel Chemicals cat. N° DAIC14625)
Mobile phase: KPF6 100 mM/Acetonitrile-60/40
Flow: 0.8 ml/min
Temperature: 35° C.
Wavelength: UV, 215 nm Preparation of Crude Aomoxetine (S)-(+)-Mandelate Salt Example 1

To an anhydrified organic solution of crude racemic tomoxetine in toluene (TMX content: 85.37 g by HPLC assay), 8.5 ml (0.1 ml/g racemic tomoxetine) of methanol and 30.53 g of (S)-(+)-mandelic acid were added under stirring at 20° C. All solids were dissolved by heating to about 65° C., then crude mandelate salt was crystallized on cooling: the temperature was lowered from 65° C. to 45° C. in about 1 hour. Crystallization started spontaneously at around 45° C. If necessary, the reaction mixture was seeded with (R)-atomoxetine (S)-(+)mandelate. The suspension was then cooled from 45° C. to 0° C. in about 2 hours. The resulting slurry was stirred at 0° C. for 1-2 hours, then the solid was isolated by filtration and washed with 2×45 ml of toluene. Yield: 43%

(R)-tomoxetine (S)-(+)mandelate (R-TMX-SMA)/(S)-tomoxetine (S)-(+)mandelate (S-TMX-SMA): about 95/5% area by HPLC.

Preparation of Enantiomerically Pure Atomoxetine (S)-(+)-Mandelate Salt

Example 2

20 g of crude wet atomoxetine (S)-(+)-mandelate salt (0.049 mol, R/S=94.3: 5.56; containing 6.8 g of toluene), 31.7 ml of toluene and 8.27 ml of methanol (1 ml/g tomoxetine base) were mixed under stirring at about 20° C.

The suspension was heated to 65° C. for about 30 min and a solution was obtained. (R)-(−)-tomoxetine (S)-(+)-mandelate was crystallized on cooling: temperature was lowered from 65° C. to 20° C. in 3 hours.

The slurry was stirred at 20° C. for 1 hour, then the solid was isolated by filtration and washed twice with 10 ml of toluene.

The solid was dried under vacuum to yield: R-TMX-SMA/(S-TMX-SMA): 99.91/0.09% area by HPLC.

Example 3

20 g of crude wet atomoxetine (S)-(+)-mandelate salt (0.049 mol, containing 6.8 g of toluene) and 31.7 ml of toluene were mixed under stirring at about 20° C.

The suspension was heated to 65° C. and 4.4 ml of Methanol were dropped until a solution was obtained. The temperature was then lowed from 65° C. to 20° C. in 3 hours and crystallisation immediately occured.

The slurry was stirred at 20° C. for 1 hour, then the solid was isolated by filtration and washed twice with 10 ml of toluene.

The solid was dried at 50° C. under vacuum for 18 hours to yield: R-TMX-SMA/S-TMX-SMA: 99.93/0.07% area by HPLC.

Example 4

One mole of crude dry atomoxetine (S)-(+)-mandelate salt (R/S=96.5/3.3), 1222.5 ml (total amount: 3 ml/g dry atomoxetine mandelate corresponding to 4.8 ml/g tomoxetine base) of toluene and 153.2 ml (0.376 ml/g dry atomoxetine mandelate corresponding to 0.6 ml/gTMX base) of methanol were mixed under stirring at about 20° C.

The suspension was heated to 65° C. in about 30 min and a solution was obtained. (R)-(−)-tomoxetine (S)-(+)-mandelate was crystallized on cooling: temperature was lowered from 65° C. to 20° C. in 6 hours. Crystallization started spontaneously between 55° C. and 50° C. The slurry was stirred at 20° C. for 1 hour, then the solid was isolated by filtration and washed twice with 270 ml of toluene.

The solid was dried at 50° C. under vacuum for 15 hours to obtain 323.3 g. Yield: 79.3%. R-TMX-SMA/S-TMX-SMA: 99.93/0.07% area by HPLC.

Example 5

15 g of crude dry atomoxetine (S)-(+)-mandelate salt (0.0368 mol), 45 ml of toluene and 5.64 ml of methanol were mixed under stirring at about 20° C.

The suspension was heated to 65° C. in about 30 min and a solution was obtained. (R)-(−)-tomoxetine (S)-(+)-mandelate was crystallized on cooling: temperature was lowered from 65° C. to 45° C. in 1.5 hours, kept at 45° C. for 1.5 hours, and then cooled to 20° C. in another 1.5 hours.

The slurry was stirred at 20° C. for 1 hour, then the solid was isolated by filtration and washed twice with 10 ml of toluene.

The solid was dried at 50° C. under vacuum for 15 hours to obtain 12.31 g. Yield: 82.1%. R-TMX-SMA/S-TMX-SMA: 99.92:0.08% area by HPLC.

Example 6

15 g of crude dry atomoxetine (S)-(+)-mandelate salt (0.0368 mol), 45 ml of toluene and 5.64 ml of methanol were mixed under stirring at about 20° C.

The suspension was heated to 65° C. for about 30 min and a solution was obtained. (R)-(−)-tomoxetine (S)-(+)-mandelate was crystallized on cooling: the temperature was lowered from 65° C. to 20° C. in 3 hours, then the solid was isolated by filtration and washed twice with 10 ml of toluene.

The solid was dried at 50° C. under vacuum for 15 hours to obtain 12.31 g. Yield: 82.1%. R-TMX-SMA/S-TMX-SMA: 99.90:0.1% area by HPLC.

Example 7

63.7 g of crude, wet, toluene containing, atomoxetine (S)-(+)-mandelate salt (R/S=96.3: 3.4; LOD=32.7%, corresponding to 42.9 g of dry product, 0.1053 mol), 107.5 ml of toluene and 16.1 ml of methanol were mixed under stirring at about 20° C.

The suspension was heated to 65° C. and a solution was obtained. (R)-(−)-tomoxetine (S)-(+)-mandelate was crystallized on cooling: the temperature was lowered from 65° C. to 20° C. in 3 hours.

The slurry was stirred at 20° C. for 1 hour, then the solid was isolated by filtration and washed twice with 20 ml of toluene.

The solid was dried at 50° C. under vacuum to obtain 34.92 g. Yield: 81.4%. R-TMX-SMA/S-TMX-SMA: 99.92:0.08% area by HPLC.

Example 8

20 g of crude atomoxetine (S)-(+)-mandelate salt (0.049 mol), 60 ml of toluene and 7.5 ml of methanol were mixed under stirring.

The suspension was heated to 70° C. in 30 min, and the obtained solution was kept at 70° C. for 10 min. The mixture was then cooled from 70° C. to 0° C. in 3 hours.

The slurry was stirred at 0° C. for 1 hour, then the solid was isolated by filtration and washed twice with 10 ml of toluene.

The solid was dried at 25° C. under vacuum to obtain 17.93 g. Yield: 89.6%. R-TMX-SMA/S-TMX-SMA: 99.91:0.09% area by HPLC.

Examples 9-20

Preparation of Enantiomerically Pure Atomoxetine HCl

One mole of atomoxetine (S)-(+)-mandelate (88.6% w/w by potentiometric assay) was mixed under stirring with 2037.5 ml of n-butyl acetate and 2037.5 ml of water. Keeping the temperature between 20-25° C., 1.529 moles of 30% aqueous sodium hydroxide was added, and then the phases were separated. The organic phase was washed twice with 400 ml of water, then filtered on paper and used for the next step. While stirring and maintaining the temperature between about 22° C. and about 25° C. by means of water bath cooling, 1.1435 moles of aqueous hydrogen chloride (36%) was dropped on the atomoxetine base solution obtained above. The hydrochloride then crystallized. The obtained suspension was stirred at about 25° C. for one hour; the solid was collected by filtration, and washed twice with 345 ml of n-butyl acetate. The solid collected was dried for 18 hours at 70° C. under vacuum. Enantiomeric purities are summarized in the following table:

| Experiment | (R)-(−) tomoxetine by area % HPLC | (S)-(+) tomoxetine by area % HPLC | $\alpha_D$ |
|---|---|---|---|
| Example 9 | 99.98 | 0.02 | 42.58 |
| Example 10 | 99.98 | 0.02 | 42.1 |
| Example 11 | 99.97 | 0.03 | 42.2 |
| Example 12 | 99.94 | 0.06 | 42.4 |
| Example 13 | 99.97 | 0.03 | 42.1 |
| Example 14 | 99.92 | 0.08 | 41.8 |
| Example 15 | 99.92 | 0.08 | 42.3 |
| Example 16 | 99.97 | 0.03 | 42.5 |

-continued

| Experiment | (R)-(−) tomoxetine by area % HPLC | (S)-(+) tomoxetine by area % HPLC | $\alpha_D$ |
|---|---|---|---|
| Example 17 | 99.97 | 0.03 | 42.5 |
| Example 18 | 99.98 | 0.02 | 41.6 |
| Example 19 | 99.98 | 0.02 | 42.7 |
| Example 20 | 99.99 | 0.01 | 41.8 |

Having thus described the invention with reference to particular preferred embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications. All references mentioned herein are incorporated in their entirety.

What is claimed is:

1. A pharmaceutical composition comprising a therapeutically effective amount of enantiomerically pure atomoxetine hydrochloride, wherein the level of the (S)-(+)-tomoxetine enantiomer in the enantiomerically pure atomoxetine hydrochloride is about 0.1% or less and a pharmaceutically acceptable carrier or excipient.

2. The pharmaceutical composition of claim 1, wherein the level of the (S)-(+)-tomoxetine enantiomer is about 0.03% or less.

3. The pharmaceutical composition of claim 2, wherein the level of the (S)-(+)-tomoxetine enantiomer is about 0.01% or less.

4. The pharmaceutical composition of claim 1 wherein the enantiomerically pure atomoxetine hydrochloride is prepared by a method comprising:
   (a) combining crude (R)-(−)-tomoxetine (S)-(+)-mandelate, a $C_{1-4}$ alcohol, and an aromatic solvent to form a mixture;
   (b) heating the mixture of step (a);
   (c) cooling the mixture of step (b) to allow the crystallization of enantiomerically pure (R)-(−)-tomoxetine (S)-(+)-mandelate;
   (d) recovering the enantiomerically pure R-(−)-tomoxetine (S)-(+)-mandelate;
   (e) combining the enantiomerically pure R-(−)-tomoxetine (S)-(+)-mandelate and a mixture of water and an organic solvent to obtain a two-phase system;
   (f) adding a base to the two-phase system;
   (g) separating the organic and the aqueous phases of the two-phase system;
   (h) adding HCl to the separated organic phase to produce crystalline atomoxetine HCl; and
   (i) recovering the crystalline atomoxetine HCl.

5. The pharmaceutical composition of claim 4 where the organic solvent is a $C_{1-4}$ alkyl ester.

6. The pharmaceutical composition of claim 5 where the organic solvent is n-butyl acetate.

7. The pharmaceutical composition of claim 4 where the base is sodium hydroxide.

8. The pharmaceutical composition of claim 4 where steps (e) through (h) are performed at a temperature between about 20° C. and 25° C.

9. A method of preparing enantiomerically pure (R)-(−)-tomoxetine (S)-(+)-mandelate comprising:
   (a) combining crude (R)-(−)-tomoxetine (S)-(+)-mandelate, a $C_{1-4}$ alcohol, and an aromatic solvent to form a mixture;
   (b) heating the mixture of step (a);
   (c) cooling the mixture of step (b) to allow the crystallization of enantiomerically pure (R)-(−)-tomoxetine (S)-(+)-mandelate; and
   (d) recovering the enantiomerically pure R-(−)-tomoxetine (S)-(+)-mandelate.

10. The method of claim 9 where the $C_{1-4}$ alcohol is methanol.

11. The method of claim 9 where the aromatic solvent is selected from the group consisting of toluene, benzene and xylene.

12. The method of claim 11 where the aromatic solvent is toluene.

13. The method of claim 9 where the mixture of step (a) is heated to a temperature of about 65° C. to about 70° C.

14. The method of claim 9 where a mixture of step (b) is cooled to a temperature of about 0° C. to about 45° C.

15. The method of claim 9 where a mixture of step (b) is first cooled to a temperature of about 45° C. over about 1.5 hrs, maintained at 45° C. for about 1.5 hrs, and then further cooled to a temperature of about 0° C.

16. The method of claim 9 where the cooling of step (c) occurs over about 3 hrs.

17. A method of preparing enantiomerically pure (R)-(−)-tomoxetine (S)-(+)-mandelate comprising:
   (a) combining racemic tomoxetine, a $C_{1-4}$ alcohol, an aromatic solvent, and (S)-(+)-mandelic acid to form a mixture;
   (b) maintaining the mixture of step (a) to allow the crystallization of crude (R)-(−)-tomoxetine (S)-(+)-mandelate;
   (c) recovering the crude R-(−)-tomoxetine (S)-(+)-mandelate from the mixture of step (b);
   (d) combining the recovered crude (R)-(−)-tomoxetine (S)-(+)-mandelate, a $C_{1-4}$ alcohol, and an aromatic solvent to form a mixture;
   (e) heating the mixture of step (d);
   (f) cooling the mixture of step (e) to allow the crystallization of enantiomerically pure (R)-(−)-tomoxetine (S)-(+)-mandelate; and
   (g) recovering the enantiomerically pure R-(−)-tomoxetine (S)-(+)-mandelate.

18. The method of claim 17 where the $C_{1-4}$ alcohol is methanol.

19. The method of claim 17 where the aromatic solvent is selected from the group consisting of toluene, benzene and xylene.

20. The method of claim 19 where the aromatic solvent is toluene.

21. The method of claim 17 where the mixture of step (e) is heated to a temperature of about 65° C. to about 70° C.

22. The method of claim 17 where a mixture of step (f) is cooled to a temperature of about 0° C. to about 45° C.

23. The method of claim 17 where a mixture of step (f) is first cooled to a temperature of about 45° C. over about 1.5 hrs, maintained at 45° C. for about 1.5 hrs, and then further cooled to a temperature of about 0° C.

24. The method of claim 17 where the cooling of step (f) occurs over about 3 hrs.

25. A method of preparing enantiomerically pure atomoxetine hydrochloride comprising:
   (a) combining crude (R)-(−)-tomoxetine (S)-(+)-mandelate, a $C_{1-4}$ alcohol, and an aromatic solvent to form a mixture;

(b) heating the mixture of step (a);
(c) cooling the mixture of step (b) to allow the crystallization of enantiomerically pure (R)-(−)-tomoxetine (S)-(+)-mandelate;
(d) recovering the enantiomerically pure R-(−)-tomoxetine (S)-(+)-mandelate;
(e) combining the enantiomerically pure R-(−)-tomoxetine (S)-(+)-mandelate and a mixture of water and an organic solvent to obtain a two-phase system;
(f) adding a base to the two-phase system;
(g) separating the organic and the aqueous phases of the two-phase system;
(h) adding HCl to the separated organic phase to produce crystalline atomoxetine HCl; and
(i) recovering the crystalline atomoxetine HCl.

26. The method of claim 25 where the organic solvent is a $C_{1-4}$ alkyl ester.

27. The method of claim 26 where the organic solvent is n-butyl acetate.

28. The method of claim 27 where the base is sodium hydroxide.

29. The method of claim 27 where steps (e) through (h) are performed at a temperature between about 20° C. and 25° C.

* * * * *